(12) United States Patent
Câncio de Bulhões Silva

(10) Patent No.: US 12,029,430 B2
(45) Date of Patent: Jul. 9, 2024

(54) UMBILICAL ORTHESIS PLUG

(71) Applicant: Rebecca Cristina Câncio de Bulhões Silva, Tooele, UT (US)

(72) Inventor: Rebecca Cristina Câncio de Bulhões Silva, Tooele, UT (US)

( * ) Notice: Subject to any disclaimer, the term of this patent is extended or adjusted under 35 U.S.C. 154(b) by 172 days.

(21) Appl. No.: 17/543,387

(22) Filed: Dec. 6, 2021

(65) Prior Publication Data
US 2023/0172613 A1 Jun. 8, 2023

(51) Int. Cl.
*A61B 17/00* (2006.01)
*A61B 17/12* (2006.01)

(52) U.S. Cl.
CPC .... *A61B 17/12159* (2013.01); *A61B 17/1204* (2013.01); *A61B 17/12099* (2013.01); *A61B 2017/00951* (2013.01)

(58) Field of Classification Search
CPC .......... A61B 17/12159; A61B 17/1204; A61B 17/12099; A61B 2017/00951
See application file for complete search history.

(56) References Cited

U.S. PATENT DOCUMENTS

| | | | | |
|---|---|---|---|---|
| 5,109,997 A | * | 5/1992 | Phillips | B65D 39/12 215/361 |
| 5,192,301 A | * | 3/1993 | Kamiya | A61B 17/0057 606/198 |
| 2005/0234543 A1 | * | 10/2005 | Glaser | A61B 17/12186 623/1.42 |
| 2008/0221702 A1 | * | 9/2008 | Wallace | A61B 17/12099 623/23.65 |
| 2013/0116656 A1 | * | 5/2013 | Song | A61F 13/126 604/285 |
| 2018/0008447 A1 | * | 1/2018 | Jacobs | A61B 17/1285 |

* cited by examiner

*Primary Examiner* — Steven O Douglas
(74) *Attorney, Agent, or Firm* — Kilpatrick Townsend & Stockton LLP

(57) ABSTRACT

Disclosed is an umbilical orthesis plug for an infant, child or toddler. The plug comprises a flange and a body, wherein the body is connected to the flange and wherein the body tapers in width from the flange to the end of the plug. Methods for using the plug and kits comprising the plug are also disclosed.

16 Claims, 3 Drawing Sheets

UMBILICAL ORTHESIS PLUG

FIELD OF THE INVENTION

The present invention relates generally to an umbilical orthesis plug and to methods for using the same. In particular, the present invention relates to an umbilical orthesis plug used for infants and toddlers and to methods for using the same.

BACKGROUND OF THE INVENTION

Following clamping and cutting of the umbilical cord, an umbilicus, commonly referred to as a belly button or navel is formed from the scar tissue remaining. Belly buttons serve a purely cosmetic performance with 90% of the population reporting an "innie" or belly button that does not extend beyond the natural plane of the stomach. Approximately 10% of the population has an "outie" or belly button that does extend beyond the natural plane of the stomach. "Outies" typically result from excess skin that grows around the umbilical cord during development, though there are also theories that belly button shape can also be influenced by how the umbilical cord is clamped and cut, how the cord stump is cared for after birth, or by genetics. Belly button shape may change over time, such as from an inner to an outie. In some instances, an outie belly button may be indicative of a hernia and may cause complications.

In order to aid in closing a hernia or reshaping a belly button, baby hernia belts have been described. Such belts, however, are bulky and may not stay in place. Especially as children get older, compliance with wearing the belt is problematic.

U.S. Pat. No. 5,406,964, for example, describes an umbilical girdle for securing the navel of infants, characterized by the fact that it comprises one tubular piece formed from an elastic mesh (1) and provided in its border portions with an elastic edge. The measurements of the girdle in a state of contraction and repose and its degree of elasticity adjust to the measurements of the midsection of the infant (2), so that when in use it adheres gently but firmly around the abdomen in such a way that it secures a compress (3) and the fastening clip on the stub of the umbilical cord without causing discomfort to the user. The placement and removal of the mesh is performed quickly and simply without having to wrap it around the infant's body.

Additional options for belly button shaping and/or support include a plug device. Umbilical orthesis plugs have been described in the art but they are limited to use by adults and are typically indicated for post-surgical use. For example, US Pre-Grant Publication Nos. 2013/0178873 and 2020/0170826 describe use of an umbilical splint for shaping an umbilicus after an abdominal operation. The umbilical splint may comprise an insertion portion extending in a longitudinal direction and terminating at an insertion end for insertion into the umbilicus. Furthermore, the insertion portion may comprise a bulbous section near the insertion end. The bulbous section may be operable to apply pressure to a tissue of the umbilicus after the abdominal operation. The insertion portion may have different cross-sectional shapes including circular and oval. Finally, the insertion portion may be configured to engage the umbilicus such that the umbilical splint is retained within the umbilicus.

Accordingly, a need exists for an infant and/or child umbilical orthesis device that is effective in shaping and providing support to the umbilicus which is also comfortable and easy to use.

SUMMARY OF THE INVENTION

In some embodiments, the present invention is directed to an umbilical orthesis plug for an infant, toddler, or child, wherein the plug comprises a flange and a body, wherein the body is connected to the flange and wherein the body tapers in width from the flange to the end of the plug. In some aspects, the plug contains a silicone material, such as a medical grade silicone. The flange may have a diameter of less than 30 mm. The flange may have a height of less than 4 mm. The body may have a diameter, where it is connected with the flange, of less than 20 mm. The plug may have a height of less than 25 mm. The plug may be substantially cylindrical. The body of the plug may in width from the flange to the end of the plug by at least 2 mm. In some aspects, the tapered end of the body comprises a flat surface. The plug may further comprise multiple peelable layers of adhesive adhered to the portion of the flange connected to the body of the plug, wherein at least the top layer of adhesive is covered by a liner.

In some embodiments, the present invention is directed to a kit for umbilical shaping or support, such as of an infant, toddler, or child, the kit comprising an adhesive patch and an orthesis plug. The orthesis plug comprises a flange and a body, wherein the body is connected to the flange and wherein the body tapers in width from the flange to the end of the plug. In some aspects, the plug contains a silicone material, such as a medical grade silicone. The flange may have a diameter of less than 30 mm. The flange may have a height of less than 4 mm. The body may have a diameter, where it is connected with the flange, of less than 20 mm. The plug may have a height of less than 25 mm. The plug may be substantially cylindrical. The body of the plug may in width from the flange to the end of the plug by at least 2 mm. In some aspects, the tapered end of the body comprises a flat surface. The plug may further comprise multiple peelable layers of adhesive adhered to the portion of the flange connected to the body of the plug, wherein at least the top layer of adhesive is covered by a liner. The adhesive patch may have a surface area that is greater than the surface area of the flange. The adhesive patch may comprise adhesive on each side of the patch sized to fit over the body of the plug to cover the flange. The adhesive patch may comprise a hypoallergenic pressure sensitive adhesive on a skin-facing surface. The adhesive patch may be free of latex on a skin-facing surface.

In some embodiments, the present invention is directed to a method for umbilical shaping or support for an infant, toddler, or child, the method comprising (a) inserting an umbilical orthesis plug into the umbilicus of an infant, child or toddler, and (b) applying an adhesive patch to adhere the plug to the skin surrounding the umbilicus of the infant, toddler or child, the adhesive patch having a surface area greater than that of the flange of the plug. The umbilical orthesis plug is sized for an infant, toddler, or child and comprises a flange and a body, wherein the body is connected to the flange and wherein the body tapers in width from the flange to the end of the plug. In some aspects, the plug contains a silicone material, such as a medical grade silicone. The flange may have a diameter of less than 30 mm. The flange may have a height of less than 4 mm. The body may have a diameter, where it is connected with the flange, of less than 20 mm. The plug may have a height of less than 25 mm. The plug may be substantially cylindrical. The body of the plug may in width from the flange to the end of the plug by at least 2 mm. In some aspects, the tapered end of the body comprises a flat surface. The plug may further comprise multiple peelable layers of adhesive adhered to the portion of the flange connected to the body of the plug, wherein at least the top layer of adhesive is covered by a liner. The method may further comprise: (c) removing the plug from the umbilicus of the infant, toddler, or child, (d) washing the plug, and (e) repeating steps (a) and (b) to resecure the plug.

In some aspects, the present invention is directed to a method for umbilical shaping or support for an infant, toddler, or child, the method comprising: providing an umbilical orthesis plug, the plug comprising a flange, a body, and an adhesive, wherein the body is connected to the flange and wherein the body tapers in width from the flange to the end of the plug. The adhesive may comprise multiple peelable layers of adhesive adhered to the portion of the flange connected to the body of the plug, wherein at least the top layer of adhesive is covered by a liner. The method may further comprise (a) removing the liner of the adhesive layer of the plug, (b) inserting the plug into the umbilicus of an infant, child or toddler, and (c) applying pressure to secure the adhesive layer to the skin surrounding the umbilicus of the infant, toddler or child. In some aspects, the plug contains a silicone material, such as a medical grade silicone. The flange may have a diameter of less than 30 mm. The flange may have a height of less than 4 mm. The body may have a diameter, where it is connected with the flange, of less than 20 mm. The plug may have a height of less than 25 mm. The plug may be substantially cylindrical. The body of the plug may in width from the flange to the end of the plug by at least 2 mm. In some aspects, the tapered end of the body comprises a flat surface.

In some embodiments, the present disclosure is directed to a method for umbilical shaping or support for an infant, toddler, or child, the method comprising: (a) inserting an umbilical orthesis plug into the umbilicus of an infant, child or toddler, and (b) applying a first side of a double sided adhesive patch to the portion of the flange that surrounds the body of the plug, and (c) applying a second side of the double sided adhesive patch to the skin surrounding the umbilicus of the infant, toddler or child. The umbilical orthesis plug is sized for an infant, toddler, or child and comprises a flange and a body, wherein the body is connected to the flange and wherein the body tapers in width from the flange to the end of the plug. In some aspects, the plug contains a silicone material, such as a medical grade silicone. The flange may have a diameter of less than 30 mm. The flange may have a height of less than 4 mm. The body may have a diameter, where it is connected with the flange, of less than 20 mm. The plug may have a height of less than 25 mm. The plug may be substantially cylindrical. The body of the plug may in width from the flange to the end of the plug by at least 2 mm. In some aspects, the tapered end of the body comprises a flat surface. The plug may further comprise multiple peelable layers of adhesive adhered to the portion of the flange connected to the body of the plug, wherein at least the top layer of adhesive is covered by a liner.

DESCRIPTION OF THE DRAWINGS

The present invention will be better understood in view of the appended non-limiting figures, in which.

DETAILED DESCRIPTION OF THE INVENTION

Figure 1:
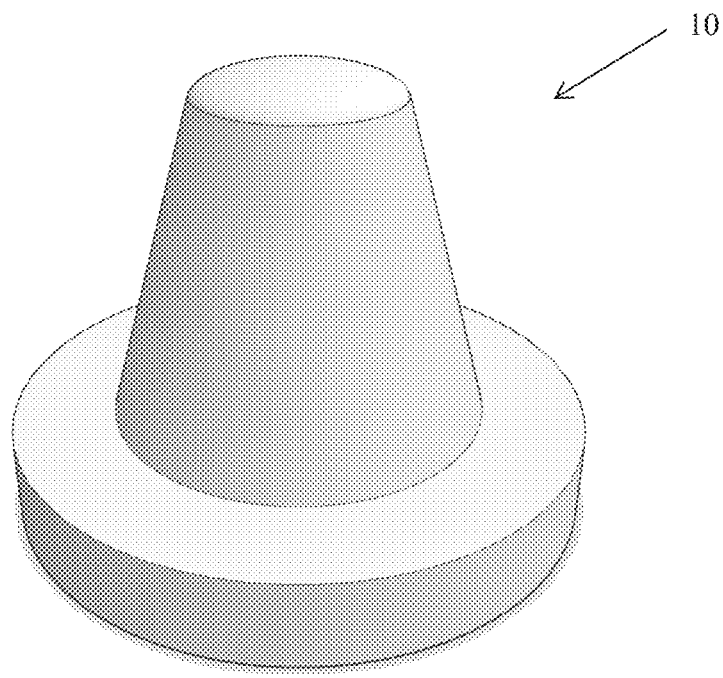
FIG. 1 provides an illustration of an umbilical orthesis plug according to aspects of the present invention.

The present invention is directed to an umbilical orthesis plug for an infant, toddler, or child. As explained above, there is a need for such plug for both medical and cosmetic reasons, especially for a plug that is easy to use and which remains in place. The plug described further herein resembles a traffic cone, and may be adhered by an adhesive. The plug comprises a flange and a body, wherein the body is connected to the flange and wherein the body tapers in width from the flange to the end of the plug. FIG. 1 illustrates an overall shape of the umbilical orthesis plug 10. Depending on the age of the user and the shape of the user's umbilicus, the size and shape of umbilical orthesis plug 10 may be tailored.

Figure 2:
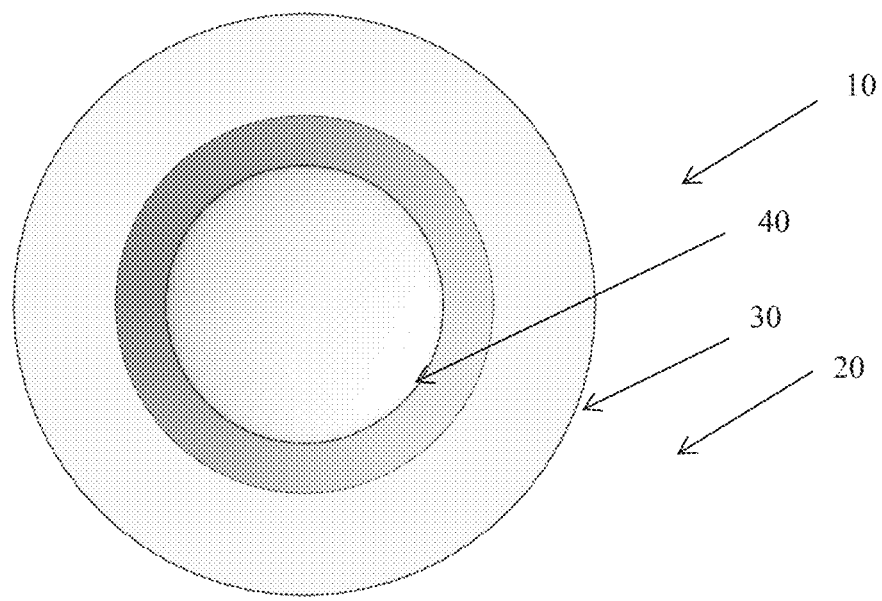
FIG. 2 provides an illustration of another view of an umbilical orthesis plug according to aspects of the present invention.
Figure 3:
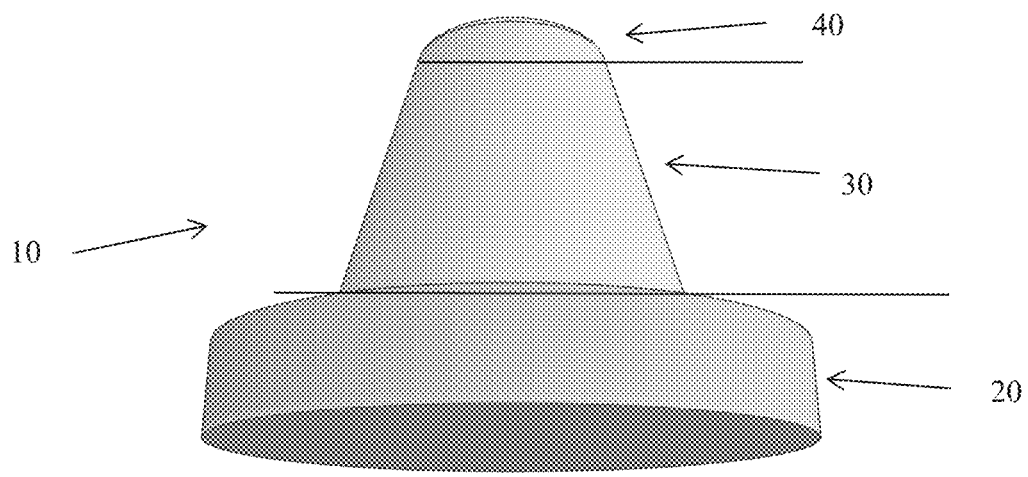
FIG. 3 provides an illustration of another view of an umbilical orthesis plug according to aspects of the present invention.

As shown in FIG. 2, umbilical orthesis plug 10 comprises a flange 20, and a body 30. The top portion of the body 40 is also shown in FIG. 2. FIG. 3 provides another view of umbilical orthesis plug 10, with the same flange 20, body 30 and top portion of body 40 shown. In some aspects, and depending on the needs of the user, the flange has a diameter, of less than 30 mm, e.g., from 10 to 30 mm, from 10 to 25 mm, from 15 to 25 mm, from 17 to 22 mm, or approximately 20 mm. In some aspects, the flange has a height of less than 4 mm, e.g., from 1 to 4 mm, from 1 to 3 mm, or approximately 2 mm. The height of the body, including the top portion of the body, may range from 12 to 24 mm, e.g., from 12 to 20 mm, from 14 to 20 mm, from 14 to 18 mm, or approximately 15 mm. The total height of the plug may be less than 25 mm, e.g., from 13 to 24 mm, from 14 to 22 mm, from 14 to 20 mm, from 14 to 18 mm, from 15 to 18 mm, or approximately 17 mm. The tapered portion of the body may comprise at least 5% of the height of the body, e.g., at least 10%, at least 15%, or at least 20%. The top portion may have a flat or rounded top and the angle of the rounded portion may range from 10 to 45 degrees.

The plug may be formed from generally acceptable materials, including silicone, particularly medical grade silicone. Medical grade silicone is washable, durable, and tolerated by most users. In some aspects, the silicone, e.g., the medical grade silicone is combined with other materials and may be present in an amount of at least 25% by weight, at least 40% by weight, at least 50% by weight, at least 75% by weight, at least 95% by weight, at least 99% by weight, or 100% by weight. In some aspects, the plug may contain additives, such as colorants, antioxidants, and scents.

As shown in FIG. 1, the plug may be substantially cylindrical. In some aspects, however, the plug need not be substantially cylindrical and may instead be more of a flattened cylinder to accommodate different user anatomy. Further, the tapered end of the plug may be modified. In some aspects, the body of the plug tapers in width from the flange to the end of the plug by at least 5% of the diameter of the widest part of the body, e.g., at least 10%, at least 15%, at least 20%, at least 25%, or at least 30%. In terms of upper limits, the body of the plug tapers by less than 80%, e.g., less than 75%, less than 70%, or less than 65%. Accordingly, the body of the plug may taper from 10 to 80%, from 15 to 75%, from 20 to 70%, from 25 to 65%, and all values and ranges included therein.

Figure 4:
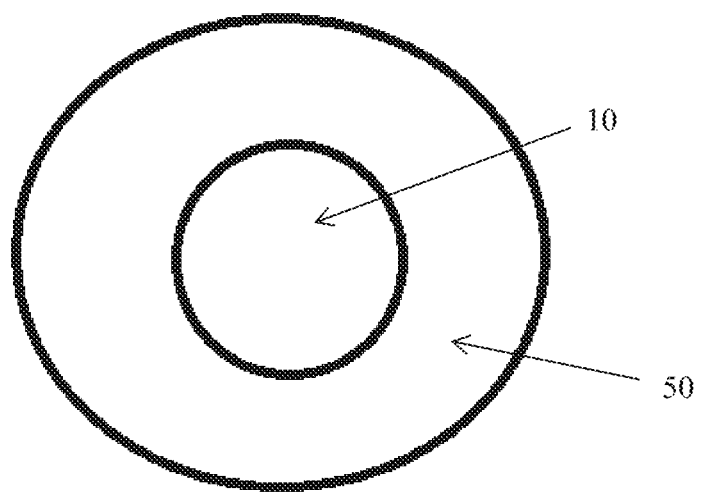
FIG. 4 provides an illustration of another view of an umbilical orthesis plug according to aspects of the present invention.

The plug may be secured to the umbilicus by any known adhesive patches, bandaids, or tape. In some aspects, the plug is secured by suppling a medical grade adhesive patch over the plug to secure the plug to the skin surrounding the flange. In some aspects, the adhesive patch has a surface area at least 5% greater than the surface area of the flange, e.g., at least 10% greater, at least 15% greater, at least 20% greater, at least 25% greater, or at least 30% greater. While there is no theoretical limit to the adhesive patch size, the plug can be efficiently secured by having a surface area of the patch of less than 100% greater than the surface area of the flange, e.g., less than 90% greater, less than 80% greater, less than 70% greater, or less than 60% greater. Thus, in terms of ranges, the surface area of the adhesive patch as compared to the surface area of the flange is from 5 to 100% greater, from 10 to 90% greater, from 20 to 80% greater, from 25 to 70% greater, from 30 to 60% greater, and all values and ranges included therein. The advantage to this configuration is that the adhesive can be removed, the plug washed, and the plug replaced with a new adhesive patch. The adhesive patch can be supplied with the plug as a kit. A patch according to this configuration is shown in FIG. 4, where adhesive patch 50 has a greater surface area than the flange of umbilical orthesis plug 10.

In some aspects, the adhesive patch may instead be included as part of the plug. In this aspect, the adhesive patch is a double sided adhesive. A first side of the adhesive is secured to the skin facing side of the exposed surface area flange. In other words, the adhesive surrounds the body where is connects to the flange. A second side of the adhesive, which will contact the skin of the user, may be covered by a liner. The adhesive patch may comprise multiple peelable layers. This configuration allows for the plug to be removed and washed, but rather than having to replace the adhesive patch as with the above embodiment, the user simply peels off a layer of adhesive to expose another layer.

The adhesive patch described herein may comprise a pressure-sensitive adhesive. Because of the sensitivity of skin of an infant, toddler, or child, the adhesive patch may comprise hypoallergenic pressure sensitive adhesives, including on a skin-facing surface of the patch. In further aspects, the adhesive may be free of latex.

Figure 5:
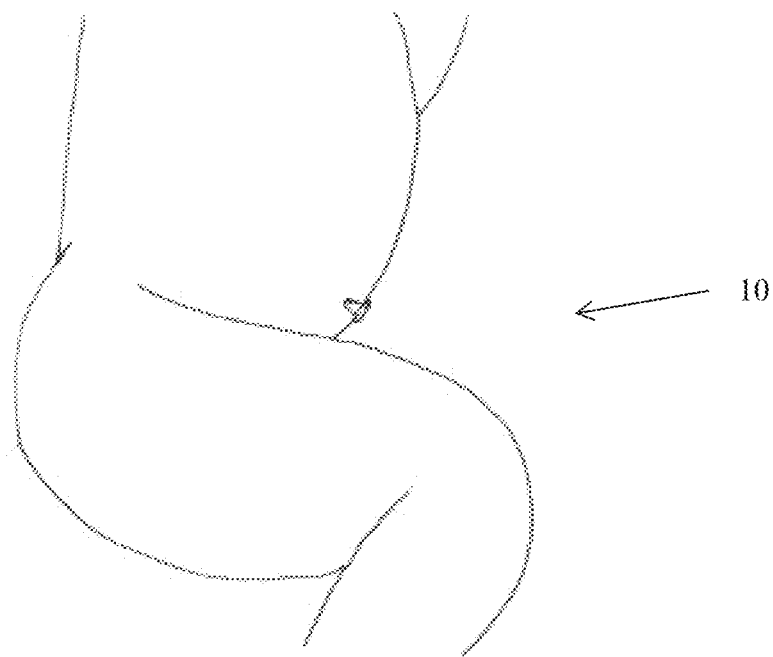
FIG. 5 provides an illustration of an umbilical orthesis plug in use according to aspects of the present invention.
Figure 6:
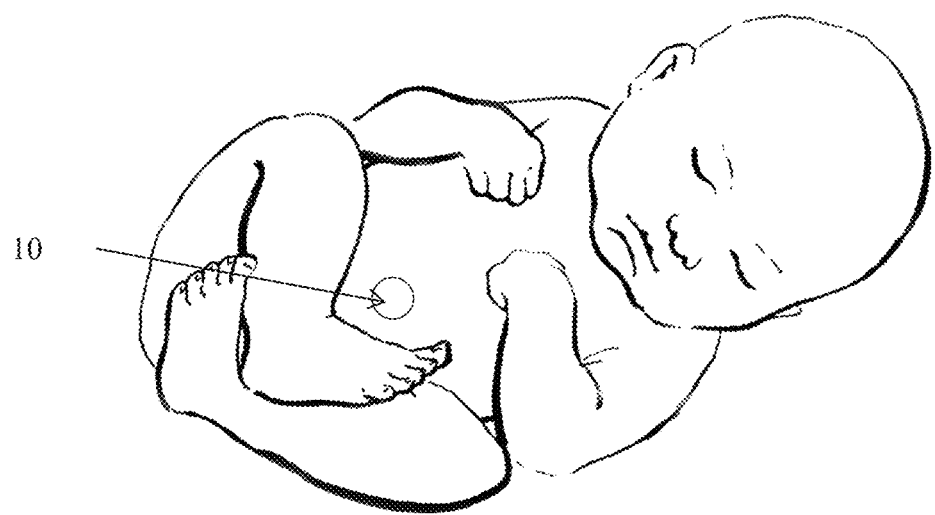
FIG. 6 provides an illustration of another view an umbilical orthesis plug in use according to aspects of the present invention.

Also contemplated by this invention are methods of umbilical shaping for an infant, toddler or child. In some aspects, the plug may also be used for umbilical support, such as umbilical surgical support, e.g., following hernia repair surgery. The method include inserting the plug, e.g., at a 90% angle, and securing the plug to the umbilicus by applying an adhesive patch over the flange and onto the skin of the user. In other methods, the method includes removing a liner from an adhesive patch on the plug, inserting the plug, and using pressure to adhere the adhesive to the user. Regardless of the method, the adhesive and plug can be removed by pressure, the plug washed, and the plug reused. The plug may be used for up to 24 hours without removing, and can be used as needed. For example, the plug can be used in an infant once the umbilical cord dries and falls off and for a period of 1 day, 3 days, 5 days, 1 week, 2 weeks, 3 weeks, 1 months, or even longer. FIG. 5 shows one view of the plug 10 as worn by the user. FIG. 6 shows another view of plug 10 as worn by the user.

The following non-limiting embodiments are contemplated:

Embodiment 1: An umbilical orthesis plug for an infant, toddler, or child, wherein the plug comprises a flange and a body, wherein the body is connected to the flange and wherein the body tapers in width from the flange to the end of the plug.

Embodiment 2: The plug according to Embodiment 1, wherein the plug contains a silicone material.

Embodiment 3: The plug according to any of Embodiments 1-2, wherein the plug contains medical grade silicone.

Embodiment 4: The plug according to any of Embodiments 1-3, wherein the flange has a diameter of less than 30 mm.

Embodiment 5: The plug according to any of Embodiments 1-4, wherein the flange has a height of less than 4 mm.

Embodiment 6: The plug according to any of Embodiments 1-5, wherein the body has a diameter, where it is connected\ with the flange, of less than 20 mm.

Embodiment 7: The plug according to any of Embodiments 1-6, wherein the plug has a height of less than 25 mm.

Embodiment 8: The plug according to any of Embodiments 1-7, wherein the plug is substantially cylindrical.

Embodiment 9: The plug according to any of Embodiments 1-8, wherein the body tapers in width from the flange to the end of the plug by at least 2 mm.

Embodiment 10: The plug according to any of Embodiments 1-9, wherein the tapered end of the body comprises a flat surface.

Embodiment 11: The plug according to any of Embodiments 1-10, wherein the plug further comprises multiple peelable layers of adhesive adhered to the portion of the flange connected to the body of the plug, wherein at least the top layer of adhesive is covered by a liner.

Embodiment 12: A kit for umbilical shaping for an infant, toddler, or child, the kit comprising an adhesive patch and an orthesis plug according to any of Embodiments 1-11.

Embodiment 13: The kit according to Embodiment 11, wherein the adhesive patch has a surface area that is greater than the surface area of the flange.

Embodiment 14: The kit according to Embodiment 11, wherein the adhesive patch comprises adhesive on each side of the patch sized to fit over the body of the plug to cover the flange.

Embodiment 15: The kit according to any of Embodiments 12-14, wherein the adhesive patch comprises a hypoallergenic pressure sensitive adhesive on a skin-facing surface.

Embodiment 16: The kit according to any of Embodiments 12-15, wherein the adhesive patch is free of latex on a skin-facing surface.

Embodiment 17: A method for umbilical shaping or support for an infant, toddler, or child, the method comprising: (a) inserting the plug of any of Embodiments 1-11 into the umbilicus of an infant, child or toddler, and (b) applying an adhesive patch to adhere the plug to the skin surrounding the umbilicus of the infant, toddler or child, the adhesive patch having a surface area greater than that of the flange of the plug.

Embodiment 18: The method according to Embodiment 17, wherein the method further comprises: (c) removing the plug from the umbilicus of the infant, toddler, or child, (d) washing the plug, and (e) repeating steps (a) and (b) of Embodiment 17 to resecure the plug.

Embodiment 19: A method for umbilical shaping or support for an infant, toddler, or child, the method comprising: (a) removing the liner of the adhesive layer of the plug according to Embodiment 11, (b) inserting the plug of and of Embodiment 1-10 into the umbilicus of an infant, child or toddler, and (c) applying pressure to secure the adhesive layer to the skin surrounding the umbilicus of the infant, toddler or child.

Embodiment 20: A method for umbilical shaping or support for an infant, toddler, or child, the method comprising: (a) inserting the plug of any of Embodiments 1-11 into the umbilicus of an infant, child or toddler, and (b) applying a first side of a double sided adhesive patch to the portion of the flange that surrounds the body of the plug, and (c) applying a second side of the double sided adhesive patch to the skin surrounding the umbilicus of the infant, toddler or child.

All patents, publications and abstracts cited above are incorporated herein by reference in their entireties. Various embodiments of the invention have been described in fulfillment of the various objectives of the invention. It should be recognized that these embodiments are merely illustrative of the principles of the present invention. Numerous modifications and adaptions thereof will be readily apparent to those skilled in the art without departing from the spirit and scope of the present invention as defined in the following claims.

What is claimed is:

1. An umbilical orthesis plug for an infant, toddler, or child, wherein the plug comprises a flange and a body, wherein the body is connected to the flange, wherein the body tapers in width from the flange to the end of the plug, wherein the plug has a flange diameter from 10 to 25 mm, a flange height of less than 4 mm, a height of the body from 12 to 24 mm, and a total height of the plug from 13 to less than 25 mm; wherein the plug consists of and is 100% by weight medical grade silicone; and wherein the plug is sized to have a height for the flange to protrude out of an umbilicus of the infant, toddler, or child.

2. The plug according to claim 1, wherein the body has a diameter, where it is connected with the flange, of less than 20 mm.

3. The plug according to claim 1, wherein the plug has a height of less than 25 mm.

4. The plug according to claim 1, wherein the plug is substantially cylindrical.

5. The plug according to claim 1, wherein the body tapers in width from the flange to the end of the plug by at least 2 mm.

6. The plug according to claim 1, wherein a tapered end of the body comprises a flat surface.

7. The plug according to claim 1, wherein the plug further comprises multiple peelable layers of adhesive adhered to the portion of the flange connected to the body of the plug, wherein at least a top layer of adhesive is covered by a liner.

8. A kit for umbilical shaping or support for an infant, toddler, or child, the kit comprising an adhesive patch and an orthesis plug according to claim 1.

9. The kit according to claim 8, wherein the adhesive patch has a surface area that is greater than the surface area of the flange.

10. The kit according to claim 8, wherein the adhesive patch comprises adhesive on each side of the patch sized to fit over the body of the plug to cover the flange.

11. The kit according to claim 8, wherein the adhesive patch comprises a hypoallergenic pressure sensitive adhesive on a skin-facing surface.

12. The kit according to claim 8, wherein the adhesive patch is free of latex on a skin-facing surface.

13. A method for umbilical shaping or umbilical support for an infant, toddler, or child, the method comprising:
    (a) inserting the plug of claim 1 into the umbilicus of an infant, child or toddler, and
    (b) applying an adhesive patch to adhere the plug to the skin surrounding the umbilicus of the infant, toddler or child, the adhesive patch having a surface area greater than that of the flange of the plug.

14. The method according to claim 13, wherein the method further comprises:
    (c) removing the plug from the umbilicus of the infant, toddler, or child,
    (d) washing the plug, and
    (e) repeating steps (a) and (b) to resecure the plug.

15. A method for umbilical shaping or umbilical support for an infant, toddler, or child, the method comprising:
    (a) removing the liner of the adhesive layer of the plug according to claim 7,
    (b) inserting the plug into the umbilicus of an infant, child or toddler, and
    (c) applying pressure to secure the adhesive layer to the skin surrounding the umbilicus of the infant, toddler or child.

16. A method for umbilical shaping or umbilical support for an infant, toddler, or child, the method comprising:
    (a) inserting the plug of claim 1 into the umbilicus of an infant, child or toddler, and
    (b) applying a first side of a double sided adhesive patch to the portion of the flange that surrounds the body of the plug, and
    (c) applying a second side of the double sided adhesive patch to the skin surrounding the umbilicus of the infant, toddler or child.

* * * * *